(12) United States Patent
Daly et al.

(10) Patent No.: US 8,715,510 B2
(45) Date of Patent: May 6, 2014

(54) METHODS AND DEVICES FOR MEASURING THE CONCENTRATION OF AN ADDITIVE

(75) Inventors: Luke J. Daly, Belle Isle, FL (US); Craig S. Alig, Orlando, FL (US)

(73) Assignee: Ferrate Treatment Technologies, LLC, Orlando, FL (US)

( * ) Notice: Subject to any disclaimer, the term of this patent is extended or adjusted under 35 U.S.C. 154(b) by 0 days.

(21) Appl. No.: 13/994,088

(22) PCT Filed: Dec. 14, 2011

(86) PCT No.: PCT/US2011/064862
§ 371 (c)(1),
(2), (4) Date: Jun. 13, 2013

(87) PCT Pub. No.: WO2012/082869
PCT Pub. Date: Jun. 21, 2012

(65) Prior Publication Data
US 2013/0284678 A1    Oct. 31, 2013

Related U.S. Application Data

(60) Provisional application No. 61/423,523, filed on Dec. 15, 2010.

(51) Int. Cl.
*C02F 1/50* (2006.01)
*G05D 11/00* (2006.01)

(52) U.S. Cl.
USPC ....... 210/749; 210/198.1; 210/96.1; 210/101; 210/758; 210/764; 210/739

(58) Field of Classification Search
USPC ............ 210/614, 621, 626, 96.1, 101, 221.2, 210/198.1, 749, 758, 764, 739
See application file for complete search history.

(56) References Cited

U.S. PATENT DOCUMENTS

| 4,376,701 | A | * | 3/1983 | Fujimoto et al. ............. 210/96.1 |
| 5,057,229 | A | * | 10/1991 | Schulenburg et al. ........ 210/743 |
| 5,466,367 | A | * | 11/1995 | Coate et al. .................. 210/96.1 |
| 2010/0227381 | A1 | | 9/2010 | Hoag et al. |
| 2010/0300975 | A1 | | 12/2010 | Pate |

OTHER PUBLICATIONS

International Preliminary Report on Patentability dated Dec. 10, 2012 in corresponding International Application No. PCT/US11/64862.
International Search Report dated Apr. 17, 2012 in corresponding International Application No. PCT/US11/64862.
Boon et al., New sustainable concepts and processes for optimization and upgrading municipal wastewater and sludge treatment. Neptune Contract No. 036845, Nov. 1, 2010, pp. 1-23.

* cited by examiner

*Primary Examiner* — Steven Bos
(74) *Attorney, Agent, or Firm* — Knobbe Martens Olson & Bear LLP

(57) ABSTRACT

An apparatus and methods for measuring the concentration of an additive are disclosed. The apparatus comprises a treatment stream (1) and a dosing stream (2). An additive is added to the dosing stream using a metering device (3). In some embodiments, the dosing stream is mixed after adding the additive using a first mixing device (4). Downstream from the metering device and the mixing device, the concentration of the additive in the dosing stream is measured using a monitor flow cell (5). In some embodiments, the dosing stream and treatment stream are combined (6) and mixed using a second mixing device (7). The concentration of the additive in the treatment stream can be calculated as a function of the volumetric flow rate ratio of the dosing stream to the treatment stream and the measured concentration of the additive in the dosing stream.

28 Claims, 1 Drawing Sheet

US 8,715,510 B2

METHODS AND DEVICES FOR MEASURING THE CONCENTRATION OF AN ADDITIVE

CROSS-REFERENCE TO RELATED APPLICATIONS

This patent application is the national phase of International Application No. PCT/US2011/64862, filed Dec. 14, 2011, which claims the benefit of priority to U.S. Provisional Patent Application No. 61/423,523, filed Dec. 15, 2010. The foregoing applications are fully incorporated herein by reference for all purposes.

BACKGROUND OF THE INVENTION

1. Field of the Invention

The present invention generally relates to methods and devices for monitoring a low concentration additive in a flowing treatment stream. In an embodiment, the present invention relates to methods and devices for monitoring the concentration of ferrate in a flowing treatment stream.

2. Description of the Related Art

Ferrate is a strong oxidant that can react with a variety of inorganic or organic reducing agents and substrates (R. L. Bartzatt, J. Carr, Trans. Met. Chem., Vol. 11 (11), pp. 414-416 (1986); T. J. Audette, J. Quail, and P. Smith, J. Tetr. Lett., Vol. 2, pp. 279-282 (1971); D. Darling, V. Kumari, and J. BeMiller, J. Tetr. Lett., Vol. 40, p. 4143 (1972); and R. K. Murmann and H. J. Goff, J. Am. Chem. Soc., Vol. 93, p. 6058-6065 (1971)). Ferrate can act as a selective oxidant for synthetic organic studies and is capable of oxidizing/removing a variety of organic and inorganic compounds from, and of destroying many contaminants in, aqueous and non-aqueous media.

Ferrate is of particular interest to water treatment because it provides a suitable mechanism for self-removal of ferrate from solution. In all oxidation reactions, the final iron product is the non-toxic ferric ion which forms hydroxide oligomers. Eventually flocculation and settling occur which remove suspended particulate matter.

The use of ferrate may therefore provide a safe, convenient, versatile and cost effective alternative to current approaches for water, wastewater, and sludge treatment. In this regard, ferrate is an environmentally friendly oxidant that represents a viable substitute for other oxidants, particularly chromate and chlorine, which are of environmental concern. Ferric oxide, typically known as rust, is the iron product of ferrate reduction. Therefore, ferrate has the distinction of being an "environmentally safe" oxidant. Although the oxidation reactions with ferrate appear similar to those known for $MnO_4^-$ and $CrO_4^{2-}$, ferrate exhibits greater functional group selectivity with higher rate of reactivity in its oxidations and generally reacts to produce a cleaner reaction products.

Previously, using ferrate in water treatment was problematic because of its lack of stability. However, recent discoveries have indicated that ferrate could be used at a site proximal to its generation, avoiding the lack of stability problem and opening up new applications. For example, U.S. Pat. No. 6,790,429, issued Sep. 14, 2004 and entitled "Methods of Synthesizing an Oxidant and Applications Thereof," the entirety of which is hereby incorporated by reference, describes methods of continuously synthesizing ferrate in a reaction chamber and delivering at least a portion of the ferrate to a site of use that is proximal to the reaction chamber. U.S. Pat. No. 6,974,562, issued Dec. 13, 2005 and entitled "Methods of Synthesizing an Oxidant and Applications Thereof," the entirety of which is hereby incorporated by reference, describes devices for continuously synthesizing ferrate for delivery to a site of use, wherein the site of use is at a distance from the output opening at which the concentration of ferrate at the site of use is equal to or greater than half the concentration of ferrate at the output opening. U.S. Pat. No. 7,476,324, issued Jan. 13, 2009, and entitled "Methods of Synthesizing a Ferrate Oxidant and its Use in Ballast Water," the entirety of which is hereby incorporated by reference, describes methods of treating ballast water and methods of synthesizing ferrate at a site where ballast water is held. It is desirable to provide devices and methods that concern the use of ferrate and other low concentration additives in water and other treatments.

SUMMARY OF THE INVENTION

The quality of a stream of water being treated by ferrate can vary over time. This change can increase or decrease the demand for ferrate, and thus, the quantity of ferrate needed for treatment of the stream. Thus, it is desirable to have a real-time measurement of the concentration of ferrate added to a stream to assure that the ferrate dose is adequate to provide the desired level of treatment.

Historically, determining the concentration of a low amount of ferrate in a treatment stream has been difficult. Many analytical methods that exist today cannot accurately measure ferrate strength. In some cases, ferrate strength can appear to be stronger or weaker than it truly is due to measurement method incompatibilities. One popular approach to ferrate strength measurement is through spectrophotometry. Ferrate absorbs light at a wavelength in the range of about 500 nm to about 520 nm, for example, at a wavelength of 510 nm. It is possible to use a spectrophotometer to measure the absorbed light and therefore determine the concentration of ferrate in a water sample. Spectrometers display absorbance measurements in terms of absorbance units (A.U.).

However, because ferrate is such a powerful treatment chemical and is costly to manufacture and use, very low doses are desirable for efficient cost-effective water treatment. In such instances, absorbance levels of ferrate using typical monitoring methods are very low. Measuring absorbance at the lower limit of the detector causes inaccuracy in the measurement because of the high noise levels. Thus, until this time it was not possible to accurately measure ferrate concentration at low concentrations. A higher concentration of ferrate would increase measurement accuracy. However, using a higher concentration, e.g. excess amounts of ferrate, dramatically increases costs.

Other more traditional methods for treating waste water, e.g. with chlorine treatment, do not have the requirements of monitoring concentrations in low doses. Because chlorine is inexpensive, an operator can use a large excess or surplus of chlorine, thus rendering precise low concentrations measurements unnecessary. Ferrate is more expensive than chlorine and it is not cost efficient to use more ferrate than is needed to effectively treat waste water. Thus, there exists a need in the art for devices that are efficient to measure low doses of ferrate concentration in a treatment stream.

Disclosed herein is a method of indirectly monitoring the concentration of ferrate in a flowing waste water stream. In one embodiment, the method comprises diverting at least a portion of the flowing waste water stream into a dosing stream. The volumetric flow rate of the flowing waste water stream and the volumetric flow rate of the dosing stream can be at a fixed ratio. In an embodiment, the method comprises adding ferrate to the dosing stream at a ferrate addition site and monitoring the concentration of ferrate in the dosing stream using a spectrophotometer downstream of the ferrate addition site. In an embodiment, the method comprises combining the ferrate-containing dosing stream with the waste water stream, wherein the ferrate enters the waste water stream.

Also disclosed, is an apparatus for monitoring low concentration ferrate in a treatment stream. In an embodiment, the apparatus comprises a treatment stream and a dosing stream that is diverted off of the treatment stream. In an embodiment, the volumetric flow rate of the dosing stream is less than the volumetric flow rate of the treatment stream. In an embodiment, a ferrate dosing pump is positioned along the dosing stream and a monitor flow cell positioned along the dosing stream at a position downstream from the ferrate dosing pump. The monitor flow cell is capable of measuring the concentration of ferrate in the dosing stream. In an embodiment, the monitor flow cell comprises a photometer.

Also disclosed, is a method of indirectly monitoring the concentration of a low concentration additive in a flowing treatment stream. In an embodiment, the method comprises flowing at least a portion of the treatment stream into a dosing stream, wherein the volumetric flow rate of the treatment stream and the volumetric flow rate of the dosing stream are at a fixed ratio. In an embodiment, the method comprises adding the additive to the dosing stream, measuring the concentration of the additive in the dosing stream and combining the additive-containing dosing stream with the treatment stream.

Also disclosed, is a method of adding a low-concentration additive to a treatment stream. In an embodiment, the method comprises flowing the treatment stream and diverting at least a portion of the treatment stream into a dosing stream, wherein the volumetric flow rate of the dosing stream is less than the volumetric flow rate of the treatment stream. In an embodiment, the method comprises adding the additive at an initial concentration to the dosing stream. The additive in the dosing stream can then be recombined with the treatment stream, such that the additive can be used in the treatment stream at low, measured doses.

Also disclosed, is a method of controlling the concentration of an additive in a treatment stream. In an embodiment, the method comprises diverting at least a portion of the treatment stream into a dosing stream, wherein the volumetric flow rate of the dosing stream is less than the volumetric flow rate of the treatment stream. In an embodiment, the method comprises measuring an initial concentration of the additive in the dosing stream using a photometer, adjusting the amount of the additive being added into the dosing stream based upon the measured initial concentration of the additive in the dosing stream, and combining the additive-containing dosing stream with the treatment stream.

Also disclosed, is a method of adding ferrate to a flowing treatment stream. In an embodiment, the method comprises adding ferrate to the treatment stream at a ferrate addition site and monitoring the concentration of ferrate in the treatment stream using a photometer downstream of the ferrate addition site.

DETAILED DESCRIPTION OF THE PREFERRED EMBODIMENT

Figure 1:
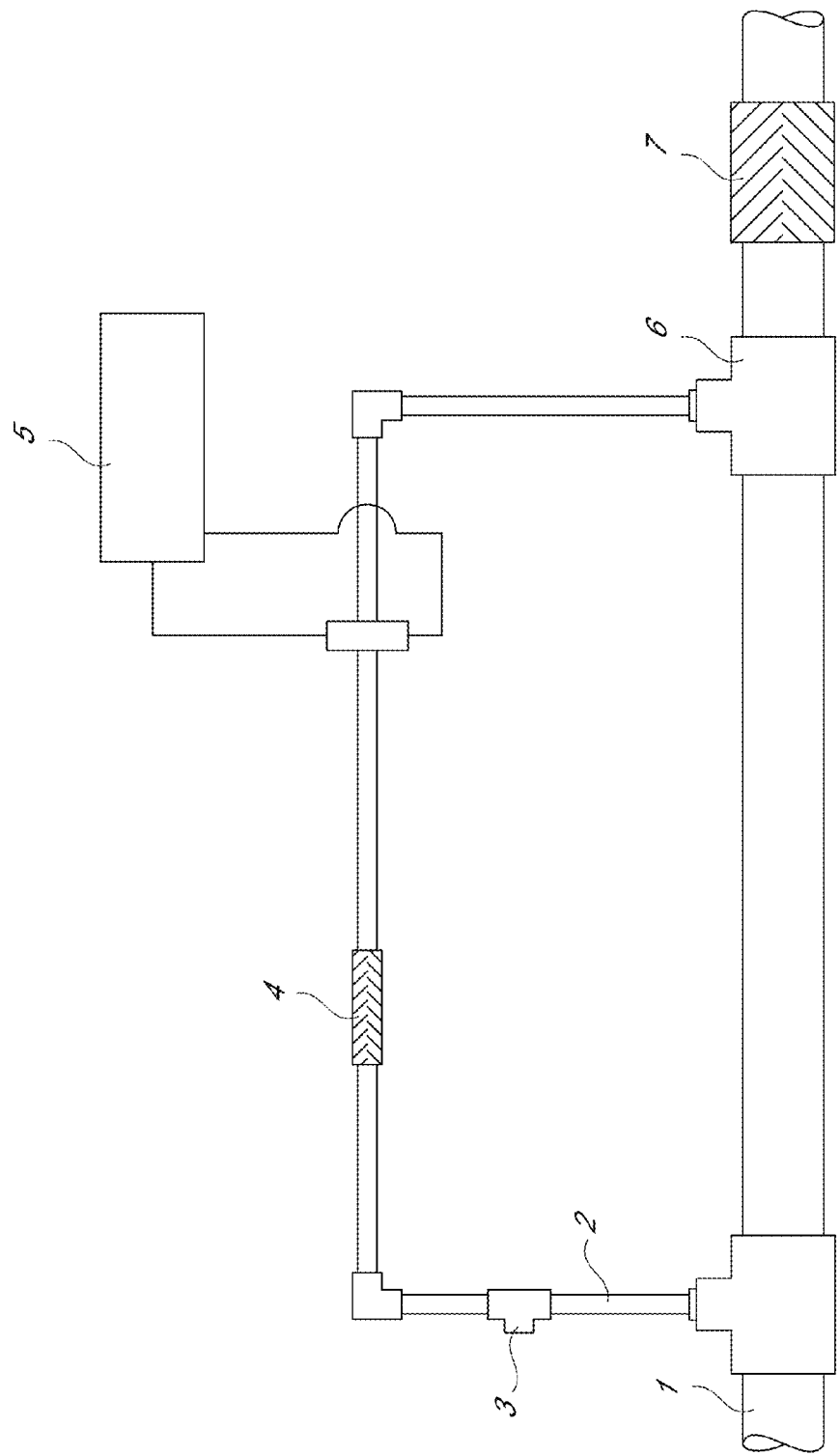
FIG. 1 depicts an embodiment of a device for monitoring the concentration of a low concentration additive.

FIG. 1 depicts an embodiment of an apparatus for monitoring a low concentration additive in a treatment stream 1. As used herein, the terms "treatment stream" or "flowing treatment stream" refer to a stream of any aqueous solution. Preferably, the aqueous solution is a water stream to be treated for purification. The aqueous solution may contain waste water, ballast water, drinking water, reuse water, process water, ground water, produced water, sea water, brackish water, storm water, combined sewer overflow, and combinations thereof.

In some embodiments, it is desirable to treat the treatment stream with an additive at a very low concentration. In fact, the concentration of the additive may be so low that it cannot be accurately measured due to excess noise. As such, an indirect method of monitoring the concentration can be employed. The additive may be any oxidant, non-oxidant, disinfectant, coagulant, flocculent or combinations thereof. Some examples of oxidants that are useful include ferrate, ozone, fluorine, chlorine, bromine, iodine, hypochlorite, chlorate, nitric acid, chromium trioxide, chromate, dichromate, permanganate, manganate, or peroxides. In an embodiment, the oxidant is ferrate. Some examples of non-oxidants include ferrous, zero valent iron, and ferric, such as ferric chloride.

While the desired concentration of an additive may be too low to be measured in the treatment stream, the same amount of additive can be accurately measured in a stream with a lower volumetric flow rate. Thus, in an embodiment, the apparatus comprises a dosing stream 2 that is diverted off of the treatment stream. The term "dosing stream" refers to a stream that is separated from the treatment stream. In some embodiments, the dosing stream is a separate pipe, but the dosing stream may also be separated from the treatment stream by any other partitioning method. The length of the dosing stream can vary. For example, those having ordinary skill in the art can vary the length of the dosing stream depending on the size of the system housing the water to be treated.

If the volumetric flow rate of the dosing stream is less than the volumetric flow rate of the treatment stream, a lesser amount of additive is required to reach a concentration that can be accurately measured in the dosing stream. The ratio of the volumetric flow rates for the treatment stream and the dosing stream can be used to calculate the additive concentration in the treatment stream after measuring the additive concentration in the dosing stream. For example, if 10 PPM of an additive is desired in a treatment stream, but the additive cannot be accurately measured below 100 PPM the volumetric flow rates of the treatment stream to the dosing stream can be configured at a ratio of about 10:1. Other volumetric flow rates could be used in this example, such as 15:1, 20:1, and 25:1. Those having ordinary skill in the art can determine the volumetric flow rate ratio in accordance with other factors, such as costs, readily available pipe sizing, and available space. If the volumetric flow rate is 10:1, then addition of the additive in an amount of 100 PPM in the dosing stream would yield a 10 PPM addition to the treatment stream. Because the concentration of 100 PPM in the dosing stream is accurately measurable, this allows one to indirectly calculate the concentration of the additive in the treatment stream downstream from where the two streams are re-combined.

In some embodiments, the volumetric flow rate of the dosing stream is preferably less than the volumetric flow rate of the treatment stream. The volumetric flow rate ratio of the treatment stream to the dosing stream can be a fixed ratio. In an embodiment, the fixed ratio is in the range of about 2:1 to about 100:1. Preferably, the volumetric flow rate ratio is in the range of about 3:1 to about 50:1. In an embodiment, the volumetric flow rate ratio is in the range of about 5:1 to about 20:1.

In an embodiment, the apparatus comprises a metering device 3 positioned along the dosing stream which is used to add an additive. In some embodiments, the metering device is a ferrate dosing pump. The ferrate dosing pump can be controlled by known computer input methods, and can be programmed to be responsive to other inputs of the apparatus.

In some embodiments the apparatus comprises a monitor flow cell 5 downstream from the metering device which can measure the concentration of the additive in the dosing stream. The monitor flow cell may comprise a photometer. In certain embodiments the photometer may comprise a spectrophotometer. When ferrate is being used as the additive, the spectrophotometer can monitor the concentration of the ferrate at a wavelength in the range of about 500 nm to about 520 nm. In an embodiment, the concentration of ferrate can be measured at a wavelength of about 510 nm. When ferrous or ferric chloride is being used as the additive, the spectrophotometer can monitor the concentration of the ferrate at a wavelength in the range of about 310 nm to about 330 nm. In an embodiment, the concentration of ferrous or ferric can be measured at a wavelength of about 320 nm.

The concentration of an additive can be more accurately measured if the additive is evenly disbursed in the dosing stream. Even distribution of the additive can be obtained using any number of mixing devices. In an embodiment, the apparatus comprise a first mixing device 4 positioned downstream from the metering device and upstream from the monitor flow cell. The mixing device may be selected from the group consisting of a mechanical mixing device, a hydraulic mixing device, and a sonic mixing device. Mechanical mixing devices include, for example, static mixers, pumps, homogenizers, or statiflo units. Hydraulic mixing devices include, for example, jets or eductors. Sonic mixing devices include, for example, sonicators.

In some embodiments, the dosing stream is re-connected to the treatment stream at a position 6 downstream from the monitor flow cell. Re-connecting the dosing stream with the treatment stream allows the additive to treat the treatment stream. In some embodiments, it is beneficial to ensure that the additive is evenly disbursed in the treatment stream. Thus, in some embodiments the apparatus comprises a second mixing device 7 positioned downstream from the point where the dosing stream is re-connected to the treatment stream to allow even mixing of the treatment stream. The second mixing device can be the same or different from the first mixing device.

Also disclosed herein is a method of indirectly monitoring the concentration of ferrate in a flowing waste water stream. As addressed, ferrate is a powerful oxidant. In some waste water treatment circumstances, the treatment concentration is so low that it cannot be detected with traditional measuring methods. However, the desired amount of ferrate can be added to a stream with a lower volumetric flow rate to allow accurate measurement at a higher relative concentration.

In an embodiment the method comprises diverting at least a portion of the flowing waste water stream into a dosing stream wherein the volumetric flow rate of the flowing waste water stream and the volumetric flow rate of the dosing stream is configured at a fixed ratio. The dosing stream is a stream that is separated from the treatment stream. In some embodiments, the dosing stream is a separate pipe, but the dosing stream may also be separated from the treatment stream by any method that partitions the two streams.

The volumetric flow rate of the dosing stream is preferably configured to be less than the volumetric flow rate of the waste water stream. As a result, less ferrate can be added to the dosing stream to reach a concentration that can be accurately measured. In an embodiment, the volumetric flow rate fixed ratio is in the range of about 2:1 to about 100:1. Preferably, the volumetric flow rate ratio is in the range of about 3:1 to about 50:1. In an embodiment, the volumetric flow rate ratio is in the range of about 5:1 to about 20:1.

In some embodiments the method comprises adding ferrate to the dosing stream at a ferrate addition site. Ferrate may be added by any method, including using a ferrate metering pump. In some embodiments the concentration of ferrate is measured in the dosing stream at a point down stream from the ferrate addition site. The concentration of ferrate is measured by any method, including a spectrometer. In an embodiment the concentration of ferrate in the dosing stream is measured substantially continuously. By measuring the concentration substantially continuously, the amount of ferrate added at the ferrate addition site can be adjusted in real time to meet varying demands.

In some embodiments, it is desirable to mix the dosing stream downstream from the ferrate addition site to allow even distribution of the ferrate in the dosing stream. The stream is mixed downstream from the ferrate addition site and upstream from the point where the concentration is measured, evenly mixing the stream prior to measuring the concentration. The dosing stream is mixed using any of the mixing devices discussed above.

In an embodiment, after the concentration is measured, the ferrate-containing dosing stream is recombined with the waste water stream, allowing the ferrate to treat the flowing waste water stream. After obtaining the concentration of ferrate in the dosing stream, the concentration of ferrate in the waste water stream can be calculated indirectly as a function of the concentration of the ferrate in the dosing stream and the ratio of the volumetric flow rates of the waste water stream and the dosing stream. Accordingly, the concentration of ferrate in the waste water stream can be calculated even if the concentration is lower than what could be accurately measured directly. After the concentration of ferrate in the waste water stream is indirectly calculated, the amount of ferrate added can be adjusted in real time to meet current demands. For example, the monitor flow cell can measure the amount of ferrate or other additive in the dosing stream and communicate with the metering pump that is administrating the additive to adjust the addition rate.

Also disclosed herein is a method of indirectly monitoring the concentration of a low concentration additive in a flowing treatment stream. In some applications, the additive concentration is so low that it cannot be detected with traditional measuring methods. However, the desired amount of additive can be added to a stream with a lower volumetric flow rate to allow accurate measurement at a higher relative concentration. In some embodiments the method comprises flowing at least a portion of the treatment stream into a dosing stream and adding an additive to the dosing stream.

The flowing treatment stream may be a stream of any aqueous solution. The aqueous solution may contain waste water, ballast water, drinking water, reuse water, process water, ground water, produced water, sea water, brackish water, storm water, combined sewer overflow, and combinations thereof. A dosing stream is a stream that is separated from the treatment stream. In some embodiments, the dosing stream is a separate pipe, but the dosing stream may also be separated from the treatment stream by any partitioning method. The additive may be, but is not limited to, any oxidant, non-oxidant, disinfectant, flocculent or coagulant or combinations thereof. Some examples of oxidants that are useful include ferrate, ozone, fluorine, chlorine, bromine, iodine, hypochlorite, chlorate, nitric acid, chromium trioxide, chromate, dichromate, permanganate, manganate, or peroxides. In an embodiment, the oxidant is ferrate. Some examples of non-oxidants include ferrous, zero valent iron, and ferric, such as ferric chloride.

In some embodiments the method comprises measuring the concentration of the additive at a point downstream from where the additive was added to the dosing stream. The concentration may be measured using a photometer. In some embodiments the photometric measurement of the additive concentration is performed using a spectrophotometer. In an embodiment, the spectrophotometer is configured at a wavelength that corresponds to the additive. Preferably, the measurement is performed using a spectrophotometer at a wavelength in the range of about 290 to about 350 nm or about 480 to about 540 nm. More preferably the measurement is performed using a spectrophotometer at a wavelength in the range of about 310 to about 330 nm or in the range of about 500 nm to about 520 nm. In some embodiments, the concentration of the additive in the dosing stream is measured substantially continuously.

Also disclosed is a method of controlling the concentration of an additive in a treatment stream. It is difficult to control the concentration of an additive when the desired concentration is so low that it cannot be accurately measured. In some embodiments, the method comprises diverting at least a portion of the treatment stream into a dosing stream. The dosing stream allows the user to add an additive to the dosing stream, accurately measure its concentration, and control that concentration prior to mixing the dosing stream with the treatment stream. Then, the amount of additive added to the dosing stream may be adjusted to control the concentration of the additive in the treatment stream.

In an embodiment, the low concentration additive is ferrate. In some embodiments ferrate is added to the treatment stream at a ferrate addition site. In certain embodiments, the concentration of the ferrate in the treatment stream is monitored using a photometer downstream of the ferrate addition site.

The embodiments described above may be used in conjunction with any use for ferrate to increase the efficiency of measurement and, by extension, the overall efficiency of the process. Discussed below are only some of the potential uses of ferrate and the manner in which the invention increases the efficiency of said use.

Uses of Ferrate

Generally, ferrate can be used in connection with any known process and for any known purpose. Ferrate is especially useful as an oxidant, flocculent and/or coagulant. In particular, potential uses of ferrate include the following: removal of color from industrial electrolytic baths; manufacture of catalysts for the Fischer-Tropsch process to produce reduced hydrocarbons from carbon monoxide and hydrogen; purification of hemicellulose; selective oxidation of alkenes, alkyl side chains, organic sulfur compounds, thiols, sulfinic acids, organic nitrogen compounds, carboxylic acids, halides, alcohols and aldehydes and in oxidative coupling; as a general oxidant for water, waste water and sewage treatment; disinfection as a biocide or virocide; phosphorylase inactivator; anti-corrosion paint additive; denitration of flue gas; electrodes for batteries; detoxification of cyanide and thiocyanate from waste waters; oxygen demands measurement; cigarette filters to remove HNC and carcinogenic molecules; oxidizer for hazardous wastes and other waste solutions such as from the pulp industries; pollution control in the removal of hydrogen sulfide from low pressure gas streams; removal of pollutants with mutagenic and carcinogenic characters such as naphthalene, nitrobenzene, dichlorobenzene and trichloroethylene from waste water and drinking water without coproduction of harmful products; additive to cements as structural hardener; disinfectant to inactivate *E. coli, Salmonella, Shigella*, and other fecal coliform as a bacterial cell removal step; removing *Streptococcus* and *Staphylococcus*; biofouling control with non-corrosive oxidant for removal of slime films formed of microorganisms such as in electric power plants and shipboard cooling systems; removal of bacteria, heavy metals and inorganics in drinking water in an oxidation coagulation processes; removal of hydrogen sulfide from sour gas in the "Knox" process; delignification of agricultural residues to produce glucose and ethanol from wheat straw; magnetic filler of barium and strontium ferrate for flexible plastics having high polymer binder contents; support for other oxidizers such as chromium (VI) and $KMnO_4$; denitrification of sinter furnace off-gas; removal of impurities from solutions fed to zinc plants; decontamination of waste waters containing cyanide and thiocyanate; oxidative destruction of phenol, sulfite and thiosulfate; as a catalyst in burning of coal to remove impurities in steam gasification step; component of grinding wheels; etching agent in fluid form for evaporated films; and ceramic encapsulated rare earth metal ferrates for use in electronics where ferromagnetic properties are needed. These and other applications are discussed in Deininger, U.S. Pat. Nos. 5,202,108, 5,217,584, and 5,370,857, all of which are incorporated herein by reference in their entirety.

Additional uses of ferrate are discussed below.

A. Waste Water Treatment

As noted above, there is a need for development of safe, inexpensive and "environmentally friendly" oxidants, especially for water and wastewater treatment applications. The treatment of industrial and municipal effluents containing hazardous organic and inorganic compounds is an important research endeavor. Currently, several methods for contaminant removal exist, including adsorption, coagulation, biodegradation, chemical degradation, and photodegradation. Chemical degradation is often the most economically feasible as well as the easiest method for water treatment and usually involves chlorine, hypochlorite, or ozone. Although effective, these oxidants often have deleterious side effects. Chlorine and ozone are poisonous and highly corrosive gases.

Hypochlorite is generally supplied as a solid or in aqueous solution; however, it is generated using chlorine gas and can rapidly decompose back into chlorine upon heating or chemical mishandling. Also, although hypochlorite, $OCl^-$, is used as a chlorine source for water treatment at smaller operations, it is expensive.

Additionally, the handling of chlorine, or hypochlorite, poses potential danger to workers due to its high toxicity. A major disadvantage of chlorine and chlorine-containing oxidants is that excess chlorine can produce chlorinated oxidation products (e.g., chloramines, chlorinated aromatics, chlorinated amines or hydrocarbons), many of which are potential mutagens or carcinogens, and may be more toxic than the parent contaminants and/or more difficult to remove. Because these compounds potentially constitute a health hazard for the public, a move away from chlorine use is needed.

Ferrate may be used in treating waste water, sewage, or sludge. It is well known in the art that ferrate reacts with organic or inorganic compounds and biological entities, such as cells, bacteria, viruses, etc. In this reaction, the substrates are oxidized to biologically inactive products. The ferrate molecule itself is reduced to Fe(III), which precipitates out of the solution as $Fe(OH)_3$ or other Fe(III) salts. The iron containing salts can be easily filtered out, leaving iron-free water containing innocuous by-products.

*Escherichia coli, Salmonella*, and *Shigella* are all members of the Enterobacteriaceae. These bacteria and certain others known to those of skill in the art have similar physiological characteristics, including being rod shaped gram-negative facultatively anaerobic organisms. *E. coli* has long been used as an indicator of fecal pollution in water systems and there is a large volume of disinfection literature available for this particular organism. Ferrate is an effective biocidal agent against suspended bacterial cultures in clean systems. Ferrate has the capacity to rapidly inactivate several known pathogens at fairly low concentrations.

Ferrate is also an effective disinfectant against viruses, such as the F2 virus. Ferrate has been studied for its antiviral activities and has been found to be effective in inactivating viruses (Kazama, Wat. Sci. Tech. 31(5-6), 165-168 (1995).) Ferrate also coagulates turbidity in water system and inactivates most enteric pathogens at ferrate concentrations which are reasonable for use in a water and wastewater treatment facility.

The biocidal properties of ferrate have also been investigated (Y. Yamamoto, Mizu Shori Gijutsu, Vol. 24, p, 929 (1983)). An important property of ferrate toward its application as a water treatment agent is its ability to act as a potent biocide. Ferrate has been used for disinfection in river water treatment, as well as in municipal sewage treatment processes; with its use, removal of coliform bacteria depends on the pH. It has been shown to be effective against *E. coli* and *sphaerotilus* (F. Kazama, J. Ferment. Bioeng., Vol. 67, p. 369 (1989)). Ferrate has also been used to remove coliform bacteria from treated sewage and river water (F. Kazama and K. Kato, Hamanashi Daigaku Kogakubu Kenkyu Hokoku, Vol. 35, p. 117 (1984)).

In addition, ferrate can be used to oxidize ammonia in the secondary effluent from water treatment plants. The major oxidation product is nitrogen, while some nitrites are also present in the products. Both of these oxidation products are environmentally friendly.

The above properties of ferrate can be exploited at municipal or industrial water treatment plants. A ferrate producing device can be installed in close proximity of the water treatment facility. Waste from the municipal sewer lines or the industrial effluent lines is mixed with freshly produced ferrate on site. The ferrate producing device can produce as much or as little ferrate as is necessary to react with all the waste present in the effluent.

Because ferrate is an efficient disinfectant, it has potential for use in lieu of extensive chlorination of drinking water. As pollution increases, the need exists for a water purifying agent that can be safely used by the individual on "small" quantities of drinking water as well as at the municipal/industrial wastewater level. Such purification agents should ideally be able to disinfect and remove suspended particulate materials, heavy metals (including radioisotopes) and some organics through flocculation, in order to at least partially destroy dissolved organic contaminants through oxidation, and as a final step, to remove itself from solution. A one-step purification reagent which meets these criteria is $FeO_4^{2-}$, ferrate. This ion is able to successfully compete with the current two-step, chlorination/ferric sulfate, flocculation technique, thereby circumventing the production of toxic or carcinogenic halogenated organics.

Because ferrate has multipurpose oxidant-coagulant properties, it is very attractive for the treatment of waste produced by chemical and pharmaceutical companies. These companies spend billions of dollars per year in clean up costs for contaminated water used, or produced, in their processes. Nearly all of the waste produced by these companies can be oxidized to relatively harmless by-products by ferrate, leaving water that can be released to the municipal sewage systems and be treated without any special care. Thus, any company that produces waste water laced with organic, inorganic, or biological impurities can install a ferrate producing device at the end of its effluent line.

Municipal sewage systems suffer a special burden. They are overloaded with any imaginable waste, most of which is organic or biological. Once the large objects are filtered out, the sewer facilities must deal with the soluble waste remaining behind. Normally, waste water facilities filter the waste water through activated charcoal or other filters that have an affinity for organic compounds, or biologically treat the wastewater. These processes are slow and costly. The slow response of these facilities to the in-flow of wastewater often results in sewer overflows during storms. In coastal communities this results in raw and untreated sewage spilling into the ocean or lake nearby, causing environmental damage. While oxidants may easily be used to remove the unwanted waste rapidly, the oxidants currently available on the market are either cost prohibitive, or produce by-products that are at times more environmentally unsafe than the waste itself.

Also, there is a vital need for new methods for $H_2S$ control in municipal sanitary sewer systems and treatment plants, and industrial waste treatment facilities. One of the ongoing major problems in waste water treatment is severe corrosion of facility structures from contact with hydrogen sulfide gas, $H_2S$, or its oxidation products after contact with air. Equally important are the health risks from exposure to $H_2S$ gas for even short periods of time; such exposure is reported to be the leading cause of death among sanitary sewer workers. Another major problem with the evolution of $H_2S$ gas is its foul smell that causes discomfort to those exposed to it.

Ferrate is known to be useful in a variety of waste water treatment applications. Ferrate oxidations, and their application to waste water treatment, have been studied with a view toward using ferrates in several industrial applications, in particular with a number of organic and inorganic substrates. (J. D. Carr, P. B. Kelter, A. Tabatabai, D. Spichal, J. Erickson, and C. W. McLaughlin, Proceedings of the Conference on Water Chlorination and Chemical Environmental Impact Health Effects, pp. 1285-88 (1985)). The applicability of ferrate in waste treatment involves not only its oxidative abilities, but also other multipurpose properties, such as its floc formation, disinfective properties, and generally remediative faculties.

Direct filtration of ground water using ferrate has been examined at the pilot plant level (T. Waite, Environ. Sci. Technol., Vol. 17, p. 123 (1983)). Biofouling control has been investigated (R. L. Bartzatt and D. Nagel, Arch. Env. Health, 1991, Vol. 46(5), pp. 313-14 (1991)). The coagulative properties of ferrate have been found to be useful for turbidity removal (S. J. de Luca, C. N. Idle, A. C. Chao, Wat. Sci. Tech. 33(3), 119-130 (1996)). Studies have shown that when model condensers were dosed with $10^{-5}$ M solutions of ferrate twice a day, for 5 minutes, biofilm growth was inhibited (T. Waite, M. Gilbert, and C. Hare, Water Tech/Qual., pp. 495-497 (1976)).

Ferrate oxidative destruction of nitrosamines, which are potent carcinogens, in waste water has been reported (D. Williams and J. Riley, Inorg. Chim. Acta, Vol. 8, p. 177 (1974)).

Relatively low ferrate doses have been found to profoundly reduce the BOD (biological oxygen demand) and TOC (total organic carbon) in domestic secondary effluents (F. Kazama and K. Kato, Kogabkubu Kenkyu Kokou, Vol. 35, pp. 117-22 (1984)).

Ferrate can be employed for the treatment of mill effluent and sewage sludge from municipal sources. Treatment at 125-1000 mg of $K_2FeO_4$/L dose levels was found to significantly decrease the chemical oxygen demand on manganese ($COD_{Mn}$), due to partial oxidation of the high molecular weight organics. Decreases in the UV spectrum after treatment with ferrate have been interpreted as removal of fulvic and humic acids within the iron(III) coagulate produced when the ferrate was reduced (F. Kazama and K. Kato, Kogabkubu Kenkyu Kokou, Vol. 34, pp. 100-4 (1984)).

Polyaminocarboxylates such as diethylenetriaminepentaacetate (DTPA), ethylenediaminetetracetate (EDTA), and nitriloacetate (NTA) are synthetic ligands that form stable complexes with most of the metals and are used in a variety of industrial applications such as photographic developing, paper production, and textile dyeing. Ethylenediaminedisuccinic acid (EDDS) forms hexadentate chelates with transition metals and is used in consumer products, e.g., washing powder. EDTA is a constituent of formulations for chemical decontamination of the primary heat transport system of nuclear power reactors. The presence of heavy metals, along with polyaminocarboxylates has been reported at many US Department of Energy (DOE) sites. These polyaminocarboxylates are either poorly biodegradable (e.g., EDTA), associated with other safety regulatory issues (e.g., NTA) or little effective (e.g., citrate). Ferrate can be applied to degrade polyaminocarboxylates and metal-polyaminocarboxylates to simple products.

Certain compounds are listed in the EPA Contaminant Candidate List (CCL). These include diazion, disulfoton, fonofos, terbufos, cyanazine, prometon, 1,2-diphenylhydrazine, nitrobenzene, acetochlor, 2,4,6-trichlorophenol, and 2,4-dichlorophenol. These compounds can be oxidized by ferrate.

The gasoline additive methyl tert-butyl ether (MTBE) is a ubiquitous groundwater contaminant. The U.S. geological Survey National Water Quality Assessment Program has identified it in 27% of urban wells tested. A more recent survey indicated that between 5 and 10% of all community drinking wells in the United States have detectable MTBE contamination. It persists in petroleum-contaminated aquifers. MTBE in groundwater can be oxidized to relatively non-hazardous compounds using ferrate.

Trichloroethene (TCE), a nonflammable solvent used in large quantities in industry, is one of the most common organic ground water contaminants and is classified as a "probable human carcinogen." TCE is sequentially reduced to dichloroethene (DCE) isomers, chloroethene (CE), and ethene. The use of ferrate in remediating contaminated groundwater is attractive due to ease of field implementation and the relatively low cost.

Highly chlorinated phenol derivatives, such as pentachlorophenol (PCP) have been listed as a priority pollutant by the United States Environmental Protection Agency. PCP is mainly used as a wood preservative and general biocide. PCP is a suspected carcinogen and its pyrolysis and combustion reaction products are considerably more toxic than PCP itself. Ferrate can be utilized in degradation of PCP.

Ferrate can also be applied to effluent streams from agrochemical industry. One of the common products from an agricultural industry, the herbicide trifluaraline is a pre-emergent, cellular and nuclear division inhibitor. It is highly toxic for humans. Ferrate can be applied to effluent streams of agrochemical industry containing compounds such as trifluraline.

Dyes present in wastewater, which originated from the textile industry, are of particular environmental concern since they give undesirable color to the waters. They are also generally harmful compounds and can lead to toxic byproducts through hydrolysis, partial oxidation, or other chemical reactions taking place in the waste phase. The decolorization and degradation of different classes of textile dyes from the textile industry can be achieved using ferrate.

In pharmaceutical and fine chemical manufacturing, organic transformations are routinely carried out using oxidizing agents based on transition metal compounds. One of the biggest problem areas in synthetic methodology is selective oxidations. For example, the oxidation of alcohols carried out with Cr(VI) or Mn(VII) lack specificity and selectivity. Ferrate is selective and specific in these reactions. The nontoxic properties of the Fe(III) byproduct makes ferrate an environmentally safe oxidant. Ferrate can be utilized in organic synthesis, thereby reducing the environmental impact of the oxidation processes and also reducing their cost ("green chemistry").

Thiourea and its derivatives are known corrosion inhibitors and are used as chemical complexing agents to clean scales developed in industrial equipment, like boilers and nuclear reactors. Because of the toxicity of thiourea to aquatic organisms, the treatment of boiler chemical cleaning wastes (BCCWs) is required before their disposal. Ferrate can easily remove thiourea and its derivatives from BCCWs.

Oil refineries and coke processing plants generate sulfur and cyanide containing compounds. These contaminants are toxic and environmentally significant due to their offensive odor. In addition, their presence may not be acceptable in the environment due to their high oxygen demand. Ferrate can be applied to petroleum industry effluents to eliminate odor related to sulfur and cyanide containing compounds.

Drinking water supplies are sometimes plagued by odors resulting from the presence of manganese(II). Manganese(II) causes aesthetic problems such as colored water, turbidity, staining, and foul taste. Manganese(II) can also accelerate biological growth which further exacerbates odor problems. Mn(II) is removed by oxidation of soluble Mn(II) with a ferrate to sparingly soluble hydroxide and oxide solid phases, MnOOH(s) and $MnO_2$(s), respectively.

Decontamination of chemical warfare agents is required on the battlefield as well as in pilot plants, and chemical agents production, storage, and destruction sites. Ferrate can oxidize chemical warfare agents such as VX [O-ethyl-S-(2-diisopropylamino)ethylmethylphosphono-thioate], GD (pinacolyl methylphosphonofluoridate), GB (2-propylmethylphosphonofluridate), mustard gas (2,2'-dichlorodiethyl sulfide), and HD [bis(2-chloroethyl)sulfide]. Ferrate has many applications such as environmentally friendly "hasty" decontamination on the battlefield where speed and ease of application of the decontaminant is essential.

During recovery of natural gas and crude oil from offshore and onshore production operations, produced waters are generated, containing complexed mixtures of organic and inorganic materials. Approximately, 12 billion barrels of produced water are produced in the US annually. This large volume causes major environmental problems. The water toxicity and organic loading generally characterize the impact of produced water to the environment. The treatment with ferrate can reduce the organic loading and acute toxicity of the oil field produced water.

Water supplies containing arsenic compounds are a worldwide health concern. Tens of thousands of people already show symptoms of arsenic poisoning. A maximum of ten microgram/L of arsenic in water is the threshold value recommended by the World Health Organization and the European Community. Current removal procedures are not adequate to meet criteria for ambient arsenic in water supplies. Steps involving oxidation, adsorption, and precipitation can be carried out by ferrate in removing arsenic from water.

In recent years, there has been increasing concern for the presence of natural organic matter (NOM) in potable surface and ground water supplies. One reason for concern is related to the formation of disinfection byproducts (DPB's) from the treatment of water by chlorination methods. Oxidation of NOM by chlorination produces chlorinated hydrocarbons, many of which are known or suspected carcinogens. Ferrate has excellent potential to serve as an environmentally friendly remediation treatment for reducing levels of DPB's in drinking water. This process would not form toxic chlorinated organics and may also effectively mineralize NOM to carbon dioxide, potentially eliminating the production of DPB's entirely.

Ferrate solution can be used to develop a method for protecting iron and steel castings from corrosion. This procedure is based on the formation of ferric oxide from the decay of the thin film of ferrate on the metal. In this procedure, a mixture of alkaline metal ferrate and alkaline solution containing a reducing agent is brought into contact with metal surfaces.

There are several disadvantages of using metal salts such as alum, ferric chloride, and ferrous sulfate in removing solids from a solution. First, binding of water to the metal ions creates a gelatinous sludge with a high water content that increases dewatering costs. Second, the water becomes more acidic after the addition of salts, causing a decrease in the coagulant property of the salt. Thirdly, the formation of metal-phosphate complexes causes phosphate levels in the solution to decrease and, as a result, phosphate becomes less available to bacteria. This upsets the biological function of the system. Synthetic organic polymers are used as common coagulants and flocculents to replace metal salts. To achieve this end, a large quantity of polymer is required, which makes the process expensive. There are also several disadvantages to using a synthetic polymer. Synthetic polymers release toxic materials into water due to solubility of polymers. In addition, solubility is also greatly influenced by environmental factors such as temperature and pH. Polymers are very sensitive to the quality of water and also have little effect on BOD. A combination of polymers and ferrate can be advantageous. This combination can require less amount of coagulant and thus be cost-effective. Polymer-ferrate complexes can be formed to eliminate the toxicity from the solubility of polymers. Polymer-ferrate complexes can also have multi-purpose properties and can be less sensitive towards quality of water.

As discussed above, low concentrations of ferrate are needed to effectively treat the types of water discussed above. However, as this concentration cannot be reliably monitored using conventional methods. Without a method of reliably detecting ferrate at such low concentrations, operators are required to use higher concentrations of ferrate than necessary, which increases costs dramatically. The invention disclosed herein allows an operator to monitor the concentration of ferrate at the low concentration required for treatment, resulting in substantial cost savings.

B. Treatment of Recreational Water

Ferrate can be used in pool and spa applications. It is well known that pools, Jacuzzis, and spas become polluted with organic waste. The waste enters the water from the body of the swimmers or by wind or insects. If left untreated, the water becomes turbid and foul. Usual methods of treatment include the addition of oxidants such as bleach and anti-bacterial or anti-fungal agents. These treatments create unwanted side-effects. The oxidants that are left in the water have an adverse effect on the skin of the swimmers using the water. In addition, the oxidants create environmentally harmful by-products, such as chlorinated hydrocarbons.

Ferrate may be used to treat a stream of pool water using the methods disclosed herein whereby all the organic waste is oxidized to innocuous products, the iron salts are filtered away, and the clean water is re-introduced into the pool. This represents a highly effective and cost-efficient method of cleaning the pool water, since ferrate is less costly in the long run than purchasing the numerous oxidants and anti-fungal chemicals necessary to treat a pool. The device of the present invention can be fitted to any swimming pool or Jacuzzi treated with ferrate such that the concentration of ferrate may be accurately monitored in real time at the low concentrations required for treatment.

C. Use in Processing Plants

Many processing plants generate aqueous streams comprising biosolids such as proteins, carbohydrates, fats, and oils which must be treated to remove the potentially valuable biosolids products before the stream can be discharged from the plant. These aqueous streams are often derived from food processing plants and have solids contents of about 0.01% to 5% on a weight basis. Using ferrate provides a process for clarification of such streams, whereby the solids are flocculated, and biosolids are optionally separated from the solids. The biosolids can subsequently be used, for example, in animal feeds.

As defined herein, to "flocculate" means to separate suspended biosolids from a stream comprising biosolids, where the biosolids become aggregated and separate to the top or bottom of the stream in which the biosolids had previously been suspended. Flocculation produces a flocculated material, which, if desired, can be physically separated from the stream. It is desirable to maximize the size of the flocculated material in order to facilitate removal of this material from the stream.

The aqueous stream to be treated can be from any processing plant that produces an aqueous stream comprising biosolids, such as food processing plants. For example, animal slaughterhouses and animal processing plants and other food processing plants may produce aqueous streams comprising protein, fats and oil. Animal slaughterhouses and processing plants include those for cattle, hogs, poultry and seafood. Other food processing plants include plants for vegetable, grain and dairy food processing plants for processing soybeans, rice, barley, cheese, and whey; plants for wet-milling of starches and grains; as well as breweries, distilleries and wineries. Biosolids present in aqueous streams from these processes may include sugars, starches and other carbohydrates in addition to protein, fats, and oils. For example in processing soybeans, proteins are extracted into an aqueous stream from which they are subsequently recovered.

While this invention is useful in conventional food processing operations, which produce aqueous suspensions of biosolids, it should be recognized that this invention is also useful in treatment of aqueous suspensions of biosolids derived from processing of food (animal or vegetable) materials, which may have non-food end uses. For example, when separated and recovered, proteins are useful in certain cosmetics and other skin care formulations; starch has numerous non-food uses, including uses in paper manufacture. Further still, this invention is useful to treat in general, any aqueous stream comprising biosolids, which may result from non-food processing operations. Moreover, though the biosolids, as disclosed above, are generally suspended in a substantially aqueous stream, the concentration of biosolids dissolved in the stream depends on the properties of the stream or the biosolids such as, for example, pH, salinity, or other parameters.

The process involves treatment of an aqueous stream containing biosolids, for example, proteins, to reduce suspended solids (as measured by turbidity) and optionally to separate the biosolids. The biosolids can be recovered for subsequent use. It should be recognized that this process can capture both suspended biosolids as well as soluble materials, such as those present in blood and sugars.

The flocculated biosolids can optionally be separated from the treated stream by conventional separation processes such as sedimentation, floatation, filtering, centrifugation, decantation, or combinations of such processes. The separated biosolids can subsequently be recovered and used in numerous applications. It has also been surprisingly found that the recovered biosolids from this process have reduced odor when dry relative to those recovered from a process using ferric chloride as part of a flocculating system. The flocculated biosolids can be separated and recovered by known techniques, such as those mentioned above.

The device of the present invention can be fitted to any aqueous stream containing biosolids treated with ferrate such that the concentration of ferrate may be accurately monitored in real time at the low concentrations required for treatment, further reducing costs.

E. Use in Radioactive Clean Up

The present invention is also useful for the precipitation of radioactive materials, particularly uranium, dissolved in aqueous solutions. The dissolved radioactive materials may be from a naturally flowing stream, or a uranium mining operation water treatment plant. The water from the stream is destined to be treated by a conventional city water treatment facility for drinking and home use.

Ferrate has been proposed as a treatment agent for the removal of radionuclides (transuranics) from waste water. To date, the focus has been on the nuclear industry, where ferrate is used to remove uranium and transuranic elements from contaminated water. In addition, there is currently an interest in using ferrate in the removal of plutonium and americium from waste water effluent.

U.S. Pat. No. 4,983,306 to Deininger discloses a method for transuranic element polishing from radioactive wastewater using $FeO_4^{2-}$ that involves adjusting the pH of a transuranic element-containing water source to a range of 6.5-14.0. Supposedly, removal occurs by co-precipitation of the transuranics within the ferric hydroxide matrix similar to other heavy metals. Also, small amounts of a chemical are used compared to common technology. Based on chemical dosages, radioactive sludge generation using this method is reduced by 3-20%, depending on the suspended solids content in the wastewater feed (Deininger, et al., Waste Manage. '90, vol. 1, pp. 789-795 (1990)).

The device of the present invention can be fitted to any stream containing radioactive materials treated with ferrate such that the concentration of ferrate may be accurately monitored in real time at the low concentrations required for treatment, further reducing costs.

F. Use in Treating Bilge Water

The restoration and maintenance of the chemical, physical and biological integrity of navigable water ways, including rivers, streams, lakes and oceans are increasingly receiving greater attention. Legislation has been enacted and regulations promulgated requiring certain procedures and establishing standards for restoring and maintaining the chemical, physical and biological integrity of navigable waters, including rivers, streams, lakes and oceans. One regulation governs the discharge of oil and other hazardous substances into navigable waters. Boaters and marine maintenance services are subject to such regulations due to the potential for the discharge of hazardous substances from boats, and particularly due to the potential for the discharge of contaminated bilge water.

It is periodically necessary to clean the bilge of a vessel due to the collection of stagnant, fouled, contaminated or otherwise dirty water. This stagnant, fouled, contaminated or otherwise dirty water typically includes oil, gasoline and/or diesel fuel which can create hazardous conditions and be particularly difficult to remove from the bilge. Certain laws and regulations may prohibit "discharge," which includes any spiking, spilling, leaking, or dumping of any kind of oil in any form including fuel oil, gasoline, lubricating oil and oil mixed with water in a vessel's bilge. Bilge water must be periodically pumped from the bilge of a boat. Bilge water may be fouled by a wide variety of contaminants, including motor oils, transmission, power steering and hydraulic trim fluids, fuel from the engine (gas or diesel), and solvents and paints used during repair and cleaning. Furthermore, bilge water may be contaminated with bacteria, flora, and/or fauna incompatible with the waters into which is intended to be discharged.

For this reason, bilge water is commonly cleaned or otherwise decontaminated and then the treated bilge water is removed from the bilge at a discharge station. Liquid cleaners may be used, added to the bilge water and after a short period of time, the boat is taken to a discharge station and the treated bilge water is pumped out. Such liquid cleaners do not satisfactorily break down the oil or the other organic materials and often leave an oil film in the bilge. If the liquid cleaner leaves a residue of oil, gasoline or the like, the residue contributes to the conditions which will require a subsequent cleaning and may enhance corrosion of the materials used in manufacturing the vessel. Furthermore, certain known liquid cleaners are non-biodegradable and may further contribute to the pollution problem. Thus, although systems exist for the filtrations and/or decontamination of bilge water, such in-line systems, capable of automatically cleaning and/or decontaminating bilge water prior to its discharge overboard are not sufficient to meet current needs, extremely complicated, cost prohibitive, or not widely accepted by either industry or relevant regulatory authorities.

The disclosed method may be used to accurately monitor the concentration of ferrate, and the disclosed device may be readily fitted such that, for example, bilge water may be continuously treated by low concentrations of ferrate during discharge. The bilge water may be treated on the ship or by a facility on land after it is pumped out of the ship. Ferrate, particularly in low concentrations, is less costly than purchasing numerous oxidants and other known methods of treating bilge water. This represents a highly effective and cost-efficient method of decontaminating bilge water.

G. Ballast Water Treatment Using Ferrate

The introduction of non-indigenous species into marine ecosystems by the shipping industry is an ever-increasing problem. Contamination is caused by species carried on ship hulls and in ballast water into new marine environments. Ship hull contamination has been minimized through the use of antifoulants; however transport of potentially harmful phytoplankton, microorganisms, viruses, and invertebrates in ballast water and sediments threatens marine environments throughout the world. Documentation of the introduction of aquatic nuisance species (ANS) and harmful consequences are reported in the literature and range from paralytic shellfish poisoning by dinoflagellates to European zebra mussel infestation in the Great Lakes. The resulting ecosystem impacts and environmental degradation have severe economic implications.

Ballast water is used to stabilize ships as cargo is loaded and unloaded. The volume of shipboard ballast water ranges from less than 100,000 to 14 million gallons (USEPA, 2001) or approximately 400 to 56,000 $m^3$. It is estimated that over 21 billion gallons of ballast water are discharged into US waters each year, containing as many as 10,000 marine specimens. Historically, the best practice for control of ANS has been mid-ocean exchange, which has limited effectiveness due to incomplete water removal. Some studies put the organism removal efficiency by mid-ocean exchange as low as 25% (USEPA, 2001). In addition, mid-ocean exchange can be dangerous, particularly in storm conditions, some ships are not structurally designed for ballast water exchange, it is not applicable to lake shipping, and it is difficult to verify effectiveness. A National Research Council Report and the Global Pollution Water Management Program both identify shipboard treatment processes as the most desirable approach to managing ANS(NRC, 1996; Globallast, Global Ballast Water Management Program, $1^{st}$ International Ballast Water Treatment Standards Workshop Report, IMO, London, March 2001). These treatment processes include physical separation, ultraviolet (UV) treatment, chemical biocides, heating, ultrasound, magnetic fields and a combination of these processes. A brief description of the more established technologies including physical separation, UV treatment, and biocides is provided below.

Ballast Water Treatment Options.

Proven physical ballast water treatment processes include cyclonic separation and filtration. Cyclonic separation has been shown to be quite effective at removing larger particles and biota (Glosten-Herber-Hyde Marine, "Full-Scale Design Studies of Ballast Water Treatment Systems," Prepared for the Great Lakes Ballast Technology Demonstration Project, Northeast-Midwest Institute, Washington, D.C., April 2002; Sutherland, T. F. C. D. Levings, C. C. Elliott, W. W. Hesse 2001. Effect of a ballast water treatment system on Survirvorship of natural populations of marine plankton. (*Marine Ecology Progress Series,* 210:139-148 (2001)). Centrifugal force is applied as water is forced through a vortex at high velocity. Larger material is pushed to the periphery of the spinning fluid and ejected in a reject stream (approximately 5-10% of the total flow) and discharged overboard. Advantages of this treatment process are that it involves proven technology, can be retrofitted into a ship, can be automated, and has low pumping requirements. However, it does not completely remove turbidity, which may impact downstream processes; has almost no removal capability for microorganisms, viruses, and phytoplankton; and is expensive to install.

Filtration units are frequently used for water treatment and can be designed to remove particulate matter as small as 0.01 μm. However, filters capable of removing these small materials are extremely expensive and cannot handle large flows typical of many ships. Units capable of removing particles greater than 50 μm are more applicable to shipboard operations; however, while they would effectively remove zooplankton and some phytoplankton, they will not remove microorganisms. Filter units can be automated, but the process of backwashing to remove entrained material adversely impacts ballast water pumping.

Ultraviolet treatment of ballast water has been evaluated at laboratory and pilot-scale (Sutherland et al, 2001 and Waite T. D. et al. "Removal of natural populations of marine plankton by a large-scale ballast water treatment system" *Marine Ecology Progress Series,* 258:51-63 (2003)). Again this treatment process has a proven history in standard water and wastewater applications. In laboratory studies UV treatment of cyclone treated ballast water was found to be more effective in removing bacteria and viruses than zooplankton and phytoplankton. Evidence of DNA repair during storage was observed for some phytoplankton, resulting in regrowth. Cyclone pretreatment was necessary to reduce turbidity that might otherwise interfere with UV effectiveness.

Various chemical biocides have been utilized including chlorine, glutaraldehye, SeaKleen, and acrolein (USEPA, 2001). These chemicals can be injected into ballast fill or discharge lines, thus requiring minor retrofitting of equipment. However, while these biocides are quite effective at controlling microorganisms and small zooplankton, sizeable doses are required to kill larger aquatic species resulting in high costs and potentially excessive residuals. Discharging of ballast water containing residual biocides is problematic. Physical separation is therefore necessary as a first stage treatment to reduce chemical dosage requirements.

In all cases, cost estimates suggest that shipboard treatment using current technology is orders of magnitude more expensive than mid-ocean exchange. The identification of a low-cost and highly-effective treatment approach is mandatory to prevent the spread of ANS that will have a regulatory and economic impact on worldwide shipping.

Full-Scale Implementation.

The Globallast Workshop (Globallast, 2001) has identified minimum design requirements for implementing shipboard ballast water treatment facilities. These include (1) minimal environmental impact, (2) effective in destroying target biological species, (3) safe for both the crew and the facilities, (4) compatible with ship needs and requirements, and (5) cost effectiveness. In addition other implementation considerations include the following: (1) treatment on intake or discharge, (2) regrowth potential (if the removal is less than 100%), (3) cross contamination from piping and/or tanks, (4) effects of vibration and ship movement, (5) corrosion due to salt water environment, and (6) the need for automation and minimal operator attention (Glosten-Herber-Hyde Marine, 2002). Any assessment of a ballast water treatment approach must include consideration for these requirements.

Ferrate (VI)—An Environmentally Friendly Solution.

Iron in +6 oxidation state, (ferrate), can meet these requirements economically due to its strength as an oxidant, disinfectant, and coagulant all delivered in one treatment chemical. Most importantly, its treatment by-product is non-toxic Fe(III).

Treatment of ballast water by Fe(VI) does not result in any mutagenic/carcinogenic by-products, which make ferrate an environmentally-friendly solution. Moreover, the ferric oxide produced from Fe(VI), acts as a powerful coagulant that is suitable for the removal of metals, non-metals, and humic acids (Qu, J-H, H-J. Liu, S-X. Liu, P. J. Lei. 2003 Reduction of fulvic acid in drinking water by ferrate. *J. Environ. Engg.* 129: 17-24).

Fe(VI) shows excellent disinfectant properties and can eliminate a wide variety of microorganisms at very low ferrate doses. In contrast to UV technology, ferrate inactivation to microorganisms is irreversible. Ferrate can interfere with both polymerase and nuclease activities and to degrade deoxyribonucleosides (Reddy, G. V. B. Nanduri, A. Basu, M. J. Modal. 1991 Ferrate oxidation of murine leukemiavirus reverse transcriptase: identification of the template-primer binding domain. *Biochemistry* 30: 8195-8201; Stevenson C. J. H. Davies. 1995 Potassium ferrate as DNA sequencing reagent and probe of secondary structure. *Biochem. Soc. Trans.* 23: 387S). This mechanism is responsible for unique disinfection capability of ferrate.

Removal of total and fecal coliform by ferrate in wastewater has been tested (Kazama, F. 1995 Viral inactivation by potassium ferrate. *Water Sci. Technol.* 31: 165-168; Kazama, F. 1994 Inactivation of coliphage Qβ by potassium ferrate. *J. Ferment. Bioeng.* 67: 369-373; Jiang et al. 2002). Ferrate treatment of water sources collected worldwide has achieved complete removal of total coliforms. Chlorine resistant bacteria can be easily treated with ferrate. For example, an aerobic spore-formers can be reduced up to 3-log units while sulfite-reducing clostridia are effectively killed by Fe(VI). Fe(VI) also rapidly inactivates virus f2 at low concentrations in water (Schink, T. T. D. Waite 1980 Inactivation of f2 virus with ferrate(VI). *Water Research* 14: 1705-1717). Ferrate treatment removed algae in water in conjunction with alum (Ma, J. W. Liu. 2002 Effectiveness and mechanism of potassium ferrate(VI) preoxidation for algae removal by coagulation. *Water Research* 36: 871-878).

As discussed in U.S. Patent Application Publication No. 2009/0120802A1. Preliminary ferrate disinfection tests of harbor waters were conducted at two locations in the Port of Cape Canaveral, Fla. The total coliform in Sample A was reduced to non-detectable levels with the addition of a very small ferrate dose of only 0.5 mg/L. Ferrate disinfection for *Eschericha coli* (*E. coli*) in both samples was also examined. Again, ferrate was effective in killing *E. coli* at a very low dose (0.5 mg/L). The levels of Heterotrophic bacteria in both samples A and B were also reduced to non-detectable values by ferrate at a dose of approximately 2 mg/L.

The total coliform in Sample A was reduced to non-detectable levels with the addition of a very small ferrate dose of only 0.5 mg/L. Ferrate disinfection for *Eschericha coli* (*E. coli*) in both samples was also examined. Again, ferrate was effective in killing *E. coli* at a very low dose (0.5 mg/L). The levels of Heterotrophic bacteria in both samples A and B were also reduced to non-detectable values by ferrate at a dose of approximately 2 mg/L.

The present invention may be installed to accurately monitor low concentrations of ferrate in a stream of ballast water to further reduce treatment costs by using a minimal amount of ferrate.

EXAMPLES

The examples below are non-limiting and are merely representative of various embodiments of the present disclosure.

Example 1

The following is one embodiment of a laboratory procedure for indirectly measuring ferrate concentration in a treatment stream. A dosing stream was made and the volumetric flow rate ratio of the treatment stream to the dosing stream was 25:1. Doses of ferrate in the amounts of approximately 250, 125, 62.5, 30, and 12.5 ppm were administered to the dosing stream. When rejoined to the full treatment stream, the concentration of the ferrate would be calculated to be 10, 5, 2.5, 1.2, and 0.5 ppm, respectively. Ferrate was synthesized and then diluted in a high pH buffer (to preserve ferrate strength) of a known volume. The diluted ferrate solution was then poured into a capped monitor flow cell. The monitor was then calibrated to the known concentration (ppm) of the diluted solution and verified with an analytical control. The flow cell was rinsed out with a buffer solution. Then, various doses of dilute ferrate were introduced into the monitor flow cell and then verified again with the analytical control. The goal in each case was for the monitor flow cell to achieve readings as close as possible with the analytical control. A diluted ferrate solution is meant to simulate ferrate injected into a treatment stream. The results are shown in Table 1 and FIG. 2.

TABLE 1

| Dosing stream theoretical (PPM) | Dosing stream experimental (PPM) | Treatment stream theoretical calculation (PPM) | Treatment stream experimental calculation (PPM) |
|---|---|---|---|
| 250 | 312.6 | 10 | 12.5 |
| 125 | 130.7 | 5 | 5.2 |
| 62.5 | 62.5 | 2.5 | 2.5 |
| 30 | 29.2 | 1.2 | 1.2 |
| 12.5 | 11.8 | 0.5 | 0.5 |

Example 2

A treatment stream and a dosing stream were designed having a volumetric flow rate of about 25:1. Doses of ferrate were added to the dosing stream in amounts of approximately 12.5, 25, 37.5, and 50 ppm. In the full treatment stream, this would result in calculated doses of 0.5, 1, 1.5, 2 ppm. The experiment was conducted in a similar manner as the first example. Each dose of ferrate was diluted in buffer and introduced into the monitor flow cell and then verified with the analytical control. This was done three times for each dilution. The results are shown in Table 2 and FIG. 3.

TABLE 2

| Dosing stream theoretical (PPM) | Dosing stream experimental (PPM, average of 3 measurements) | Treatment stream theoretical calculation (PPM) | Treatment stream experimental calculation (PPM) |
|---|---|---|---|
| 12.5 | 15 | 0.5 | 0.6 |
| 25 | 26.7 | 1 | 1.1 |
| 37.5 | 34.7 | 1.5 | 1.4 |
| 50 | 46 | 2 | 1.8 |

It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

Other embodiments are within the following claims.

What is claimed is:

1. A method of indirectly monitoring the concentration of ferrate in a flowing waste water stream, comprising:
    diverting at least a portion of the flowing waste water stream into a dosing stream, wherein the volumetric flow rate of the flowing waste water stream and the volumetric flow rate of the dosing stream are at a fixed ratio;

adding ferrate to the dosing stream at a ferrate addition site;
monitoring the concentration of ferrate in the dosing stream using a spectrophotometer downstream of the ferrate addition site; and
combining the ferrate-containing dosing stream with the waste water stream, wherein the ferrate enters the waste water stream.

2. The method of claim 1, further comprising the step of determining the concentration of ferrate in the waste water stream indirectly, as a function of (i) the concentration of the ferrate in the dosing stream and (ii) the ratio of the volumetric flow rates of the waste water stream and the dosing stream.

3. The method of claim 1, wherein the volumetric flow rate ratio of the waste water stream to the dosing stream is in the range of about 3:1 to about 50:1.

4. The method of claim 1, wherein the volumetric flow rate ratio of the waste water stream to the dosing stream is in the range of about 5:1 to about 25:1.

5. An apparatus for monitoring low concentration ferrate in a treatment stream, comprising:
a treatment stream;
a dosing stream that is diverted off of the treatment stream, wherein the volumetric flow rate of the dosing stream is less than the volumetric flow rate of the treatment stream;
a ferrate dosing pump positioned along the dosing stream; and
a monitor flow cell positioned along the dosing stream at a position downstream from the ferrate dosing pump, wherein the monitor flow cell comprises a photometer.

6. The apparatus of claim 5, further comprising a mixing device along the dosing stream positioned downstream from the ferrate metering pump and upstream from the monitor flow cell.

7. The apparatus of claim 6, wherein the dosing stream is re-connected to the treatment stream at a position downstream from the monitor flow cell.

8. The apparatus of claim 7, further comprising a second mixing device along the treatment stream, positioned downstream from the point where the dosing stream is re-connected to the treatment stream.

9. The apparatus of claim 8, wherein the first and second mixing devices each independently comprise a mixer selected from the group consisting of mechanical mixers, hydraulic mixers, and sonic mixers.

10. A method of indirectly monitoring the concentration of a low concentration additive in a flowing treatment stream, comprising:
flowing at least a portion of the treatment stream into a dosing stream, wherein the volumetric flow rate of the treatment stream and the volumetric flow rate of the dosing stream are at a fixed ratio;
adding the additive to the dosing stream;
measuring the concentration of the additive in the dosing stream, wherein the additive comprises ferrate, ferric iron ferrous iron, or zero valent iron; and
combining the additive-containing dosing stream with the treatment stream.

11. The method of claim 10, wherein the additive comprises one or more of an oxidant, a disinfectant, flocculent, or a coagulant.

12. The method of claim 11, wherein the additive comprises ferrate.

13. The method of claim 10, wherein the additive comprises one or more of ferric iron, ferrous iron, or zero valent iron.

14. The method of claim 10, wherein the volumetric flow rate ratio of the treatment stream to the dosing stream is in the range of about 3:1 to about 50:1.

15. The method of claim 10, wherein the volumetric flow rate ratio of the treatment stream to the dosing stream is in the range of about 5:1 to about 25:1.

16. A method of adding a low-concentration additive to a treatment stream, comprising:
flowing the treatment stream;
diverting at least a portion of the treatment stream into a dosing stream, wherein the volumetric flow rate of the dosing stream is less than the volumetric flow rate of the treatment stream;
adding the additive at an initial concentration to the dosing stream, wherein the additive comprises ferrate, ferric iron, ferrous iron, or zero valent iron; and
combining the additive-containing dosing stream with the treatment stream.

17. The method of claim 16, wherein the additive comprises one or more of an oxidant, a disinfectant, a flocculent, or a coagulant.

18. The method of claim 17, wherein the additive comprises ferrate.

19. The method of claim 16, wherein the additive comprises one or more of ferric iron, ferrous iron, or zero valent iron.

20. The method of claim 16, wherein the volumetric flow rate ratio of the treatment stream to the dosing stream is in the range of about 3:1 to about 50:1.

21. The method of claim 16, wherein the volumetric flow rate ratio of the treatment stream to the dosing stream is in the range of about 5:1 to about 25:1.

22. A method of controlling the concentration of an additive in a treatment stream, comprising:
diverting at least a portion of the treatment stream into a dosing stream, wherein the volumetric flow rate of the dosing stream is less than the volumetric flow rate of the treatment stream;
measuring an initial concentration of the additive in the dosing stream using a photometer;
adjusting the amount of the additive being added into the dosing stream based upon the measured initial concentration of the additive in the dosing stream; and
combining the additive-containing dosing stream with the treatment stream.

23. The method of claim 22, wherein the additive is an oxidant.

24. The method of claim 23, wherein the oxidant is ferrate.

25. The method of claim 22, wherein the additive is a non-oxidant.

26. The method of claim 25, wherein the non-oxidant is one or more of iron ferric, iron ferrous, or zero valent iron.

27. The method of claim 22, wherein the volumetric flow rate ratio of the treatment stream to the dosing stream during measurement of the initial concentration of the additive is in the range of about 3:1 to about 50:1.

28. The method of claim 22, wherein the volumetric flow rate ratio of the treatment stream to the dosing stream during measurement of the initial concentration of the additive is in the range of about 5:1 to about 25:1.

* * * * *

UNITED STATES PATENT AND TRADEMARK OFFICE
CERTIFICATE OF CORRECTION

PATENT NO. : 8,715,510 B2  
APPLICATION NO. : 13/994088  
DATED : May 6, 2014  
INVENTOR(S) : Luke J. Daly Page 1 of 1

It is certified that error appears in the above-identified patent and that said Letters Patent is hereby corrected as shown below:

In the Claims

Col. 22, Line 54, In Claim 26, change "iron ferric, iron ferrous," to --ferric iron, ferrous iron,--.

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,715,510 B2
APPLICATION NO. : 13/994088
DATED : May 6, 2014
INVENTOR(S) : Luke J. Daly It is certified that error appears in the above-identified patent and that said Letters Patent is hereby corrected as shown below:

In the Claims

Column 21, lines 56-57, Claim 10, change "ferric iron ferrous iron" to --ferric iron, ferrous iron--.

Signed and Sealed this
Second Day of December, 2014

Michelle K. Lee
*Deputy Director of the United States Patent and Trademark Office*